(12) United States Patent
Smith et al.

(10) Patent No.: US 10,118,028 B2
(45) Date of Patent: Nov. 6, 2018

(54) VIBRATING INSERTION TOOL

(71) Applicant: Cochlear Limited, Macquarie University, NSW (AU)

(72) Inventors: James G. E. Smith, Sydney (AU); John Thomas Roland, Jr., New York, NY (US); Frank Risi, Newtown (AU); Ben Johnston, West Pymble (AU)

(73) Assignee: Cochlear Limited, Macquarie University, NSW (AU)

( * ) Notice: Subject to any disclaimer, the term of this patent is extended or adjusted under 35 U.S.C. 154(b) by 842 days.

(21) Appl. No.: 14/063,671

(22) Filed: Oct. 25, 2013

(65) Prior Publication Data

US 2015/0119897 A1   Apr. 30, 2015

(51) Int. Cl.
| | | |
|---|---|---|
| *A61B 19/00* | (2006.01) | |
| *A61N 1/05* | (2006.01) | |
| *A61B 17/28* | (2006.01) | |
| *A61B 17/30* | (2006.01) | |
| A61B 17/32 | (2006.01) | |

(52) U.S. Cl.
CPC ............ *A61N 1/0541* (2013.01); *A61B 17/28* (2013.01); *A61B 17/30* (2013.01); *A61B 17/320092* (2013.01); *A61B 2017/320088* (2013.01)

(58) Field of Classification Search
CPC . A61B 17/28; A61B 17/29; A61B 2017/2901; A61B 2017/2932; A61B 17/30; A61B 17/320068; A61B 17/320092; A61B 2017/320088; A61N 1/0541
See application file for complete search history.

(56) References Cited

U.S. PATENT DOCUMENTS

| | | | |
|---|---|---|---|
| 4,154,228 A | 5/1979 | Feldstein et al. | |
| 5,879,363 A | 3/1999 | Urich | |
| 2004/0064151 A1 | 4/2004 | Mollenauer | |
| 2004/0238819 A1* | 12/2004 | Maghribi | ............ A61N 1/0551 257/57 |

(Continued)

FOREIGN PATENT DOCUMENTS

WO   2010/151768 A1   12/2010

OTHER PUBLICATIONS

Dictionary.com definition for "connected" as accessed Oct. 5, 2016; http://www.dictionary.com/browse/connected.*

(Continued)

*Primary Examiner* — Jonathan Miles
(74) *Attorney, Agent, or Firm* — Pilloff & Passino LLP; Martin J. Cosenza

(57) ABSTRACT

Systems and methods are disclosed for insertion of implantable medical devices, and more particularly to insertion of implantable devices with a vibrating insertion tool. More specifically, a vibrating insertion tool is described, the insertion tool comprising an insertion tool controllable by a user to support and guide movement of an object, the insertion tool comprising an elongate arm having a proximal end region and a distal end region, the distal end region having a receiving region, a user-controllable vibration source for generating vibrations in accordance with a selected vibration profile, and an elongate rigid spine, connected to the vibration source and the receiving region, configured to deliver the vibrations to the receiving region.

25 Claims, 7 Drawing Sheets

(56) References Cited

U.S. PATENT DOCUMENTS

| | | |
|---|---|---|
| 2009/0069712 A1 | 3/2009 | Mulvihill |
| 2010/0114288 A1 | 5/2010 | Haller |
| 2014/0005705 A1* | 1/2014 | Weir ............... A61B 17/00234 606/169 |

OTHER PUBLICATIONS

Merriam-Webster definition for "tweezers" as accessed Oct. 5, 2016; http://www.merriam-webster.com/dictionary/tweezers.*

Takahiro Noda et al., "Piezo-Driven Vibrating Insertion Device for Microelectrode Array," Electronics and Communications in Japan, 2011, vol. 94, No. 8, pp. 25-31.

* cited by examiner

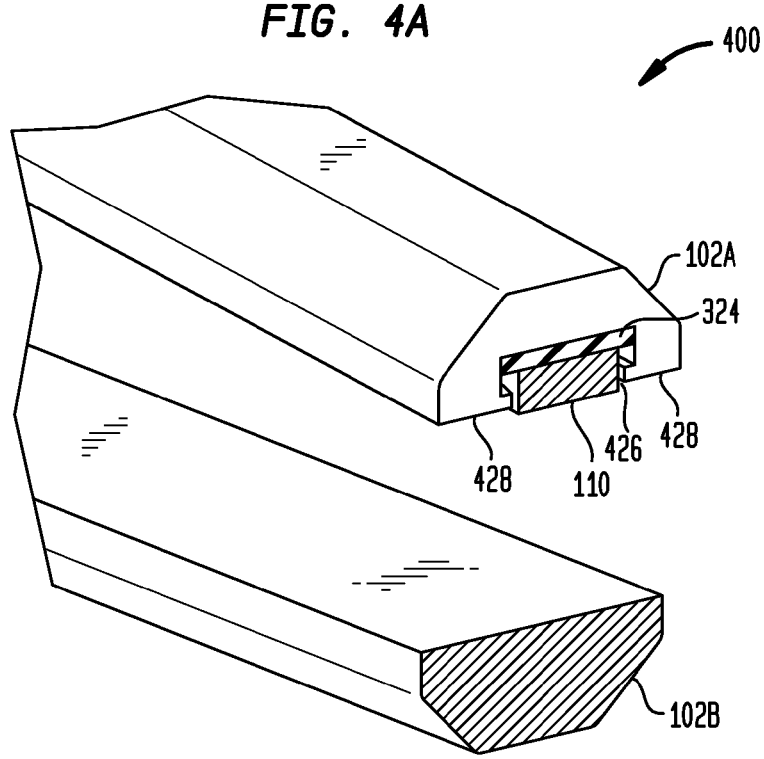
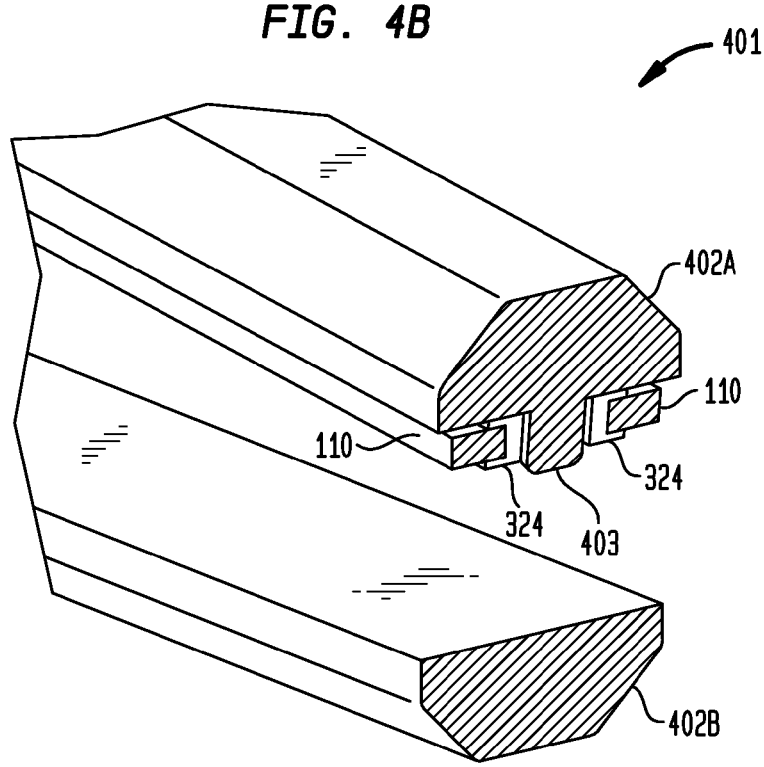

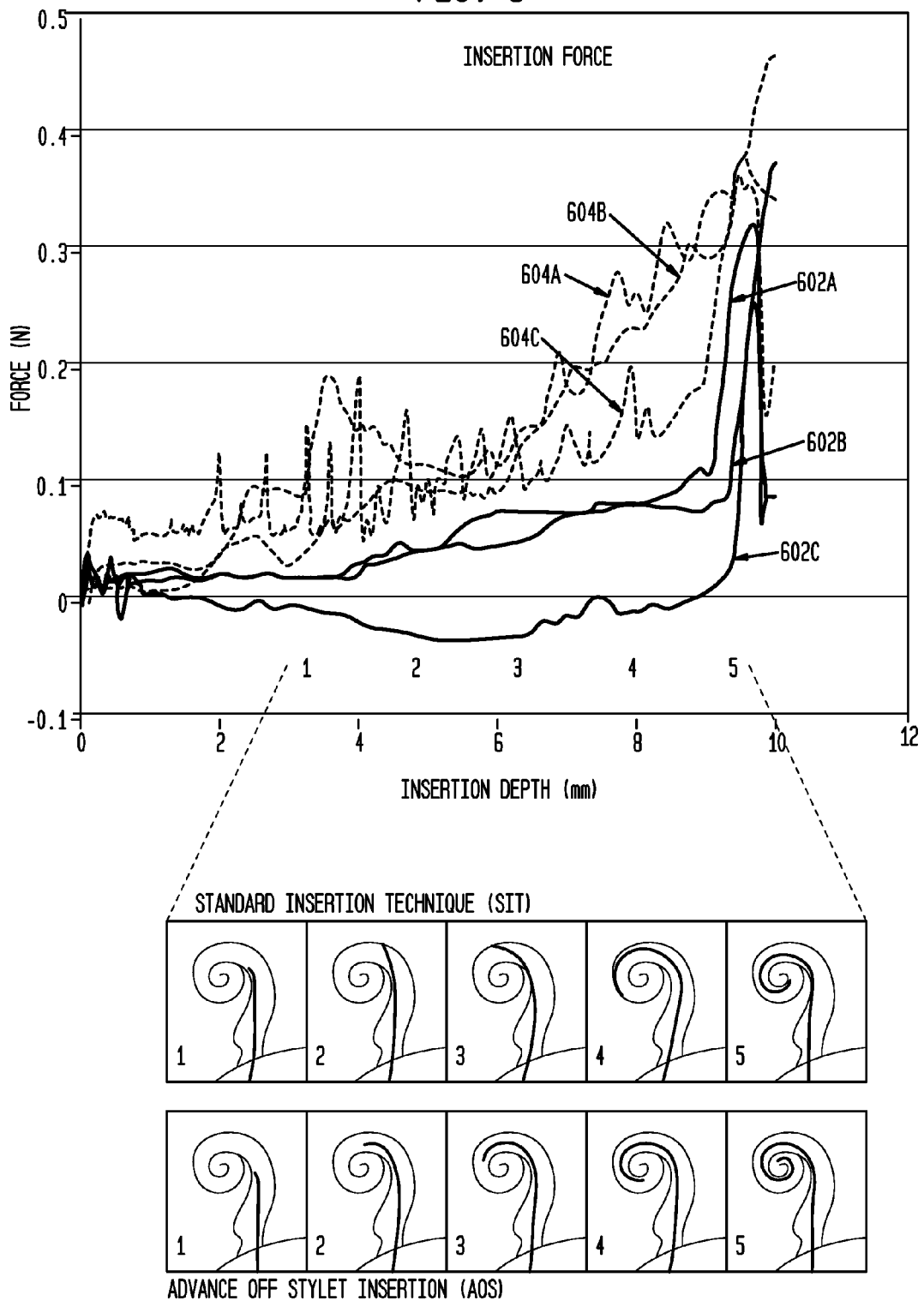

VIBRATING INSERTION TOOL

FIELD OF THE TECHNOLOGY

The present technology relates generally to insertion of implantable medical devices, and more particularly, to insertion of implantable medical devices with a vibrating insertion tool.

BACKGROUND

Hearing loss, which may be due to many different causes, is generally of two types, conductive and sensorineural. Sensorineural hearing loss occurs when there is damage to the inner ear, or to the nerve pathways connecting the inner ear to the brain. Conductive hearing loss occurs when the normal mechanical pathways that provide sound to the cochlea are impeded, for example, by damage to the ossicular chain or ear canal. However, individuals suffering from conductive hearing loss may retain some form of residual hearing because the hair cells in the cochlea may remain undamaged. As a result, individuals suffering from conductive hearing loss typically receive a hearing prosthesis that generates mechanical motion of the cochlea fluid. Still other individuals suffer from mixed hearing losses, that is, conductive hearing loss in conjunction with sensorineural hearing. Such individuals may have damage to the outer or middle ear, as well as to the inner ear (cochlea). Individuals suffering from conductive hearing loss typically receive an acoustic hearing aid. Unfortunately, not all individuals suffering from conductive hearing loss are able to derive suitable benefit from hearing aids.

Another type of hearing prosthesis is a cochlear implant. Cochlear implants provide electrical stimulation via, e.g. an electrode assembly with stimulating electrode contacts positioned as close as possible to the auditory nerve, essentially bypassing the cochlear hair cells. The application of a stimulation pattern to the nerve endings causes impulses to be sent to the brain via the auditory nerve, resulting in the brain perceiving the impulses as sound.

Insertion of a cochlear implant electrode assembly may cause trauma to the recipient's cochlea. For example, when a surgeon inserts an electrode assembly into the scala tympani, the basilar membrane may be bruised, punctured or torn. Such physical trauma may lead to a temporary or permanent change in the recipient's residual hearing characteristics.

SUMMARY

In one aspect, there is provided a vibrating insertion tool comprising: an insertion tool controllable by a user to support and guide movement of an object, the insertion tool comprising an elongate arm having a proximal end region and a distal end region, the distal end region having a receiving region; a user-controllable vibration source for generating vibrations in accordance with a selected vibration profile; and an elongate rigid spine, connected to the vibration source and the receiving region, configured to deliver the vibrations to the receiving region.

In another aspect, there is provided an integrated vibration system for an insertion tool comprising: a user-controllable vibration source for generating first vibrations in accordance with a selected vibration profile; and an elongate vibration transfer member configured to deliver second vibrations to a receiving region of the insertion tool, wherein second vibrations are delivered in accordance with substantially the same vibration profile as the selected vibration profile.

In another aspect, there is provided a method for inserting a medical device into a recipient using a vibrating insertion tool, comprising: attaching an integrated vibration system to the insertion tool; engaging the medical device with the insertion tool; inserting the medical device into the recipient; generating a control signal that defines a selected vibration profile; and generating vibrations, via the control signal, in accordance with the desired vibration profile during one or more user-defined periods during the insertion of the medical device.

BRIEF DESCRIPTION OF THE DRAWINGS

Embodiments of the present technology are described below with reference to the attached drawings, in which:

FIG. 4A is a perspective view of another exemplary vibrating insertion tool, according to embodiments of the present technology;

FIG. 4B is a perspective view of another exemplary vibrating insertion tool, according to embodiments of the present technology;

FIG. 5 is a graph that shows plots of insertion forces with respect to insertion depth applied to the cochlea structures by a non-vibrating insertion tool, and by a vibrating insertion tool according to embodiments of the present technology;

DETAILED DESCRIPTION

Figure 1A:
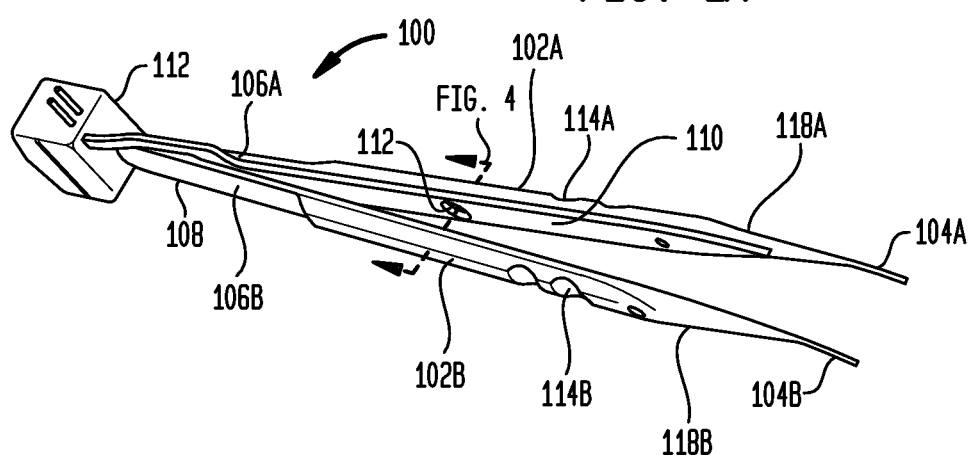
FIG. 1A is a perspective view of an exemplary vibrating insertion tool, according to embodiments of the present technology.

Aspects and embodiments of the present technology are directed to a vibrating insertion tool for inserting an implantable medical device, such as an electrode assembly, into the cochlea of a recipient.

The vibrating insertion tool includes an insertion tool with an integrated vibration system. The insertion tool may include a forceps, tweezers, surgical claws, or any other suitably configured tool that supports or receives a medical device for implantation. The vibration system includes a vibration source attached to the insertion tool, and a vibration coupling member that couples the vibration source to the tool, e.g. a distal location of the tool proximate the location of the tool that contacts the medical device. This vibration coupling member, referred to herein as, for example, a spine efficiently transfers vibrations generated by the vibration source to the region of the device that receives the medical device. In use, such vibrations are transferred to the medical device supported by the insertion tool. The vibrations from the vibrating insertion tool allow a surgeon to implant the medical device to a desired depth with a minimized insertion force, or a level of insertion force that causes less trauma to the recipient.

To efficiently deliver vibrations generated by the vibration source to the device receiving region of the insertion tool, the spine is connected to both the vibration source and a distal end of the insertion tool. Since the spine is attached to the insertion tool, contact between a surgeon using the insertion tool and the insertion tool itself may cause dampening of the vibrations traveling through the spine and may cause an unwanted effect of altering the vibration characteristics profile of the vibrating insertion tool as a whole. As such, the disclosed vibrating insertion tool includes the maximization of the decoupling or isolation of the insertion tool from the vibration-carrying spine until the spine transfers the vibrations to a specific receiving region of the insertion tool.

Furthermore, as noted, insertion forces applied to the internal structures of the cochlea can lead to cochlea trauma. Due to the vibrating of the insertion tool using the vibration source, such trauma to the cochlea of the recipient can minimized. More specifically, the inventors have further determined that implementing certain specific vibration profiles with the disclosed vibrating insertion tool helps to minimize insertion forces and as such reduce the risk of trauma. More specifically, a controller drives the vibration source to vibrate with a certain vibration profile, i.e. at a certain frequency and amplitude. During implantation, the surgeon can adjust such vibration characteristics via a user interface of the controller. Although successively higher vibration frequencies and successively greater vibration amplitudes will facilitate insertion of the medical device using successively smaller insertion forces, to ensure efficacy, a maximum vibration frequency and amplitude are enforced by the controller. In addition, the controller has vibration profiles for each of a variety of surgical circumstances, that is, the optimal vibration characteristics that enable the surgeon to implant the device using the minimal insertion force. These optimal vibration profiles vary according to the medical device, tool, fundamental frequency of the tool with the device, the surgical environment and the surgeon's manual technique, among other factors. Additional vibration profiles may be provided in the controller to accommodate each of these and other conditions.

Figure 1B:
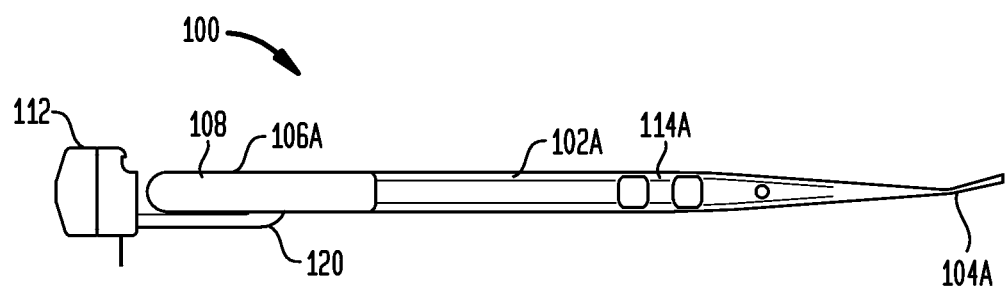
FIG. 1B is side view of an exemplary vibrating insertion tool, according to embodiments of the present technology.

FIG. 1A is a perspective view and FIG. 1B is a side view of an exemplary vibrating insertion tool 100, according to embodiments of the present technology. Vibrating insertion tool 100 includes a first arm or shaft 102A and a second arm or shaft 102B. First arm 102A and second arm 102B join together at junction 108. First arm 102A includes a tip 104A, which is located towards the distal portion 118A of first arm 102A, and second arm 102B includes a tip 104B, which is located towards the distal portion 118B of second arm 102B. Vibrating insertion tool 100 also includes a handle region or portion 114, which is divided between first arm 102A and second arm 102B. As such, first arm 102A includes handle region 114A and second arm 102B includes handle region 114B.

Vibrating insertion tool 100 is used by a surgeon to support or receive (e.g. grasp and/or hold) an object before, during or after surgery, and more specifically, for example, vibrating insertion tool 100 is used for inserting an implantable medical device, such as an electrode assembly, into the cochlea of a recipient. The surgeon may hold vibrating insertion tool 100 anywhere along handle region 114 between junction 108 and tips 104A and 104B. Tips 104A and 104B are brought together, to grasp an object, by squeezing arms 102A and 102B together until tips 104A and 104B capture the object between them.

Vibrating insertion tool 100 also includes an elongated vibration coupling member or rigid spine member 110 and a vibration source 112, as shown in FIGS. 1A and 1B. Spine member 110 is positioned between first arm 102A and second arm 102B. Spine member 110 may be shaped similarly to first arm 102A and/or second arm 102B. In such an embodiment, spine member 110 may overlap tips 104 so that when vibrating insertion tool 100 receives a medical device to be implanted, spine member 110 is in direct contact with the medical device. Spine member 110 may also be slightly shorter in length than arms 102 (such that, for example, spine member 110 extends down the length of first arm 102A and/or second arm 102B but does not overlap with tips 104, as shown in FIG. 1A). However, alternatively, spine member 110 may have a variety of other shapes, lengths and widths than those shown in FIG. 1A.

Figure 2:
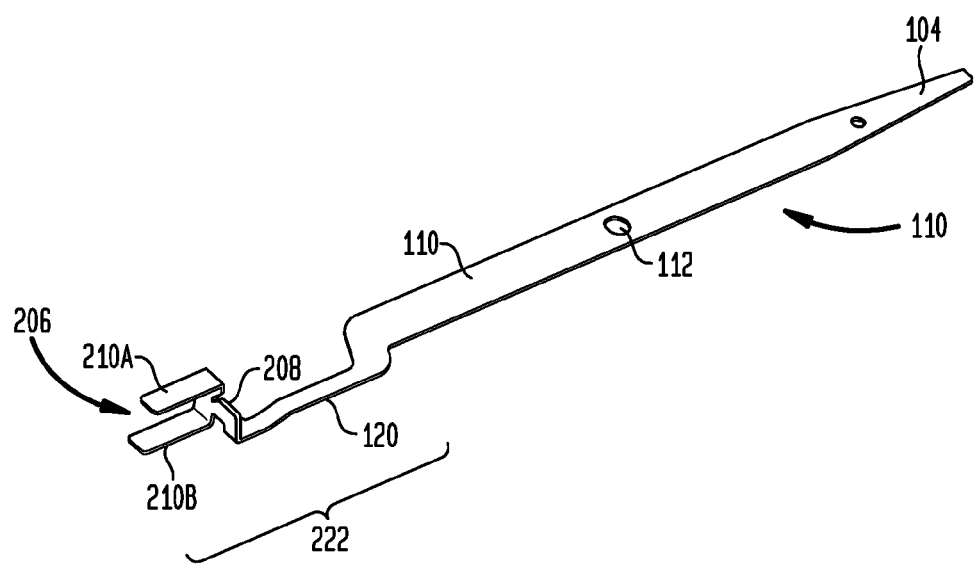
FIG. 2 is a perspective view of an elongated spine member including a dog leg shaped portion, according to embodiments of the present technology.

Spine member 110 is coupled to vibration source 112 such that vibrations from vibration source 112 are transferred to spine member 110. Spine member 110 also extends away from arms 102A and 102B so as to connect with vibration source 112. For example, spine member 110 may include a dog leg shaped portion 120 to extend beyond its location in between arms 102A and 102B, as shown in FIG. 1B and FIG. 2. According to embodiments of the present technology, vibration source 112 is connected to spine member 110 such that vibration source 112 is located towards the proximal end of vibrating insertion tool 100. It may be preferable for vibration source 112 to be located towards the proximal end of insertion tool 100 to avoid vibration source 112 from interfering with the surgeon's use of vibrating insertion tool 100 and/or avoid vibration source 112 blocking the surgeon's view of tips 104A and 104B or the surgery site during surgery. However, it should be understood that vibration source 112 may be located in various other locations with respect to vibrating insertion tool 100, including anywhere along the length of vibrating insertion tool 100 or remote from vibrating insertion tool 100 via, for example, the use of a longer spine member 110, without affecting a surgeon's use of insertion vibrating insertion tool 100. An exemplary vibration source 112 and its physical relationship with spine member 110 is discussed further with respect to FIG. 6A.

FIG. 2 is a perspective view of elongated spine member 110 including dog leg shaped portion 120, according to embodiments of the present technology. As shown in FIG. 2, spine member 110 may be connected to a vibration source holder 222 that secures vibration source 112 in place with respect to spine member 110. Vibration source holder 222 may be in the shape of a fork, such as fork 206 including plate 208 and tines 210A and 210B. In such an embodiment, vibration source 112 may be secured in between tines 210A and 210B. As such, the distance between tines 210A and 210B may be slightly smaller than the width of vibration source 112 such that tines 210A and 210B tightly hold vibrations source 112 in place.

Figure 3A:
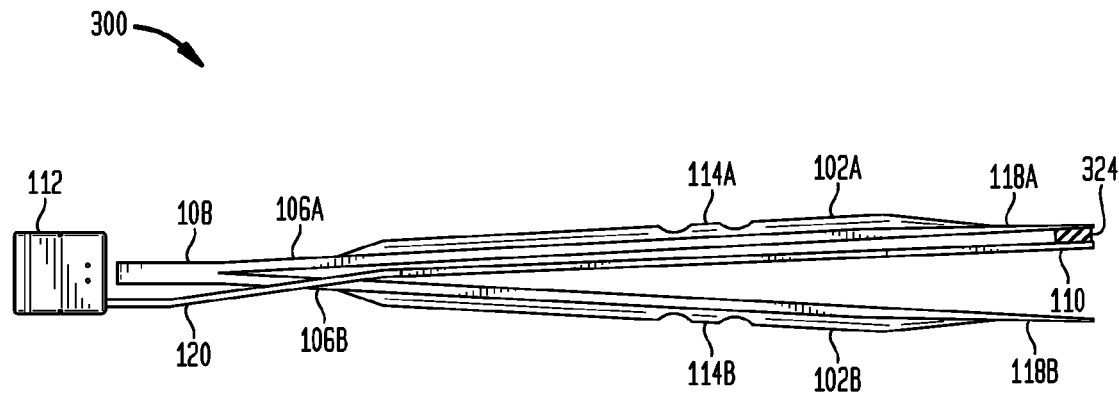
FIG. 3A is a side view of an exemplary vibrating insertion tool, according to embodiments of the present technology.
Figure 3B:
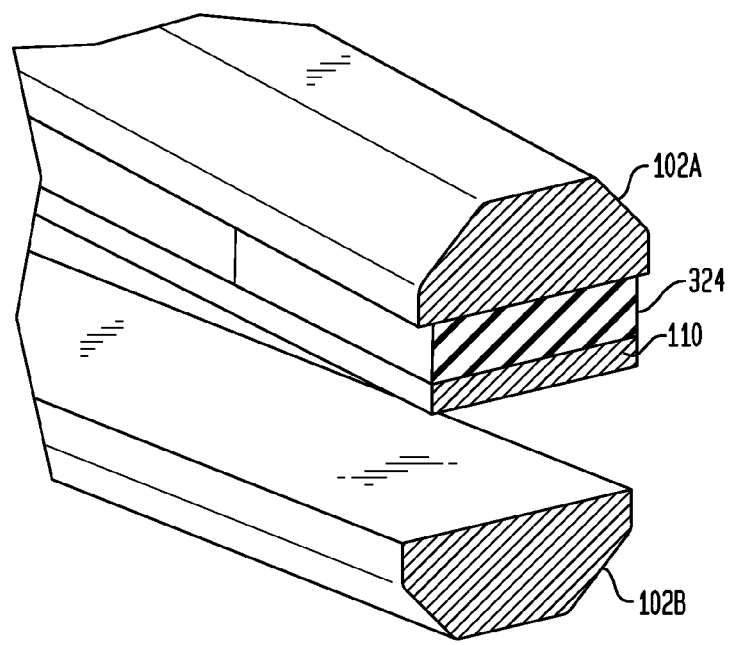
FIG. 3B is a perspective view of the exemplary vibrating insertion tool of FIG. 3A, according to embodiments of the present technology.

FIG. 3A is a side view, and FIG. 3B is a close-up perspective view, of an exemplary vibrating insertion tool 300, according to embodiments of the present technology. As shown in FIGS. 3A and 3B, spine member 110 is runs substantially parallel with arm 102A, but does not come into direct contact with arm 102A. Instead, spine member 110 and arm 102A are separated by a separator 324 (alternatively, spine member 110 may be connected to arm 102B, or there may be a second spine member connected to arm 102B). In this embodiment, separator 324 may be made of neoprene, rubber, or other elastomeric or similar material in the form of, for example, a grommet or O-ring, or any other at least semi-flexible or malleable material capable of holding spine member 110 to arm 102A and transferring vibrations from spine member 110 to arm 102A. Separator 324 used within embodiments of the present technology may also be more rigid, as will be discussed further. Separator 324 decouples, or isolates, spine member 110 from arm 102A. As noted, contact between the spine and a surgeon using the insertion tool or the insertion tool itself may cause dampening of the vibrations traveling through the spine and may cause an unwanted effect of altering the vibration characteristics profile of the vibrating insertion tool as a whole. For example, when a surgeon grasps handle portion 114, and therefore applies force to handle portion 114A of arm 102A, such dampening of any vibrations traveling through arm 102A or traveling through a member coupled to arm 102A may occur. Separator 324 allows vibrating insertion tool 100 to avoid such a rigid coupling. Since separator 324 isolates spine member 110, through which vibrations travel, from arm 102A through the portion of arm 102A at which the surgeon would grasp arm 102A, such dampening effect would be controlled and minimized or eliminated. In other words, vibrating insertion tool 300 includes a substantially unimpeded path, via spine member 110, through which to travel to the surgeon's desired receiving region. As such, vibrations being transferred by spine member 110 from vibration source 112 to the receiving region may be transferred to the implantable medical device without being substantially dampened.

Separator 324 may act as a dampener itself. However, the use of separator 324 allows for the majority of the space between spine member 110 and arm 102A to consist of empty space, or an air gap. Therefore, although separator 324 may be formed into various shapes and sizes other than those shown in, for example, FIG. 3B, it may be beneficial for separator 324 to be a small as possible while still strong enough to couple spine member 110 to arm 102A such that the dampening effect of separator 324 is as small as possible.

Furthermore, separator 324 facilitates the indirect physical coupling of spine member 110 and arm 102A. As noted, the vibrating insertion tool, and spine member 110, transfers vibrations generated by the vibration source to a specific, predetermined portion, or the receiving region, of the insertion tool. As shown in FIG. 3A, spine member 110 connects to arm 102A through separator 324 at such a specific receiving region of the insertion tool, such as, for example, tip 104A. In other words, because spine member 110 does not physically connect to arm 102A at any point except through separator 324, vibrations traveling through spine member 110 do not transfer to arm 102A at points along arm 102A other than at the selected receiving region. Since spine member 110 transfers vibrations to arm 102A at the selected receiving region of arm 102A, other portions of arm 102A (and of the rest of the insertion tool) will not directly receive vibrations and therefore may only vibrate in limited amounts due to residual vibrations that travel from the receiving region to the other portions. In other words, this permits the receiving region to vibrate together with spine member 110 substantially independently of arm 102A and the rest of the insertion tool (such as, for example, handle region 114).

Separator 324 is located, as shown in FIG. 3A for example, close to the end of arm 102A at tip 104A. However, separator 324 may be located in different positions along arm 102A, and therefore spine member 110 may be coupled to arm 102A at different positions along arm 102A. Such a position may be chosen in order to allow for the transfer of vibrations from spine member 110 to a different receiving region of arm 102A. Referring back to FIG. 1A, as shown in FIG. 1A, for example, spine 110 may be shorter than arm 102A such that spine member 110 is coupled to arm 102A at a position along arm 102A other than tip at 104A. In such an embodiment, when the vibrating insertion tool receives a medical device to be implanted, the insertion tool is in direct contact with the medical device instead of spine member 110. Therefore, vibrations transferred through spine member 110 would be transferred from spine member 110 to arm 102A, and then from arm 102A to the implantable medical device. In such an embodiment, if a separator such as separator 324 is used, separator 324 may be a rigid separator that rigidly or hard couples spine member 110 to arm 102A. For example, spine member 110 may be welded to arm 102A via separator 324. The connection between spine member 110 and arm 102A may be rigid so that vibrations being carried by spine member 110 are transferred efficiently to arm 102A and subsequently to the medical device received by the vibrating medical device and to be implanted into the recipient. FIG. 4B also provides an alternative embodiment including a spine member with a hole 112 that receives a stud 403 of arm 102A. Such an embodiment may also include a rigid connection between spine member 110 and arm 102A where the connection, and receiving region, is located on arm 102A in a location proximal to the tip of the vibrating insertion tool.

Vibrating insertion tool 300 may also include more than one separator. For example, vibrating insertion tool 300 may include a first separator that couples spine member 110 to arm 102A at tip 104A, and another separator that couples spine member 110 to arm 102A at a different predetermined position along spine member 110 and arm 102A. Using multiple separators may provide more stability for the combination of spine member 110 and arm 102A, and prevent spine member 110 from moving away from arm 102A unexpectedly when a force is applied to either spine member 110 or arm 102A, either by accident or on purpose. Furthermore, as noted, separator 324 may be formed into various shapes and sizes other than those shown in, for example, FIG. 3B. For example, the width of separator 324 may be smaller than the width of arm 102A, as shown in FIG. 4.

FIG. 4A is a close-up perspective view of an exemplary vibrating insertion tool 400, according to embodiments of the present technology. Similar to vibrating insertion tool 300 in FIG. 3A and FIG. 3B, vibrating insertion tool 400 includes arms 102A and 102B, spine member 110 and separator 324. However, vibrating insertion tool 400 differs from vibrating insertion tool 300 in that arm 102A of vibrating insertion tool 400 includes a pocket or recess 426 in which separator 324 and spine member 110 fit. Furthermore, arm 102A of vibrating insertion tool 400 may include stop members, such as stop members 428. Stop members 428 may prevent vibrating spine member 110 from moving too far in a direction perpendicular to the longitudinal axis of arm 402A.

The separator 324 shown in FIGS. 3A-4B are used to connect spine member 110 to arm 102A at the receiving region (and subsequently isolate the rest of the vibrating spine from the rest of arm 102A), a separator like material may also be used on the outside of arms 102A and/or 102B, such as on handle 114A and 114B. Such a separator may be used to isolate or decouple the surgeon's hand from directly contacting the insertion tool. Isolating the surgeon from the insertion tool may substantially reduce or prevent dampening of the vibrations transferred through the spine and may also prevent cause an unwanted effect of substantially altering the vibration characteristics profile of the vibrating insertion tool. Furthermore, such a separator may prevent vibrations from affecting the surgeon's handling during surgery.

FIG. 4B is a close-up perspective view of another exemplary vibrating insertion tool 401, according to embodiments of the present technology. Vibrating insertion tool 401 includes arms 402A and 402B. Arm 402A is similar to vibrating insertion tools disclosed herein e.g. vibrating insertion tool 100 from FIG. 1A, except that arm 402A also includes a stud protruding from the inside of arm 402A. As shown in FIG. 1A, spine 110 includes a hole 112 (although in different embodiments spine 110 may not include hole 112, such as in FIG. 3A). As shown in FIG. 4B, stud 403 of arm 402A may protrude into a hole within spine 110. The interlocking relationship between stud 403 and hole 112 allows for a physical connection between spine 110 and arm 402A. Consistent with the goal of transmitting vibrations from spine 110 to a receiving region of arm of the vibrating insertion tool, hole 112 and corresponding stud 403 may be located at or near the receiving region such that vibrations may transfer from spine 110 to stud 403 at the receiving region to, as noted, preserve the characteristics of the vibration profile of the vibrations being transferred.

As noted, insertion forces applied to the internal structures of the cochlea can lead to cochlea trauma and such trauma to the cochlea of the recipient can minimized by vibrating of the insertion tool while being used by the surgeon. FIG. 5 is a graph that shows plots of insertion forces (in Newtons), with respect to insertion depth (in millimeters), applied to the cochlea structures by a non-vibrating insertion tool and by an exemplary vibrating insertion tool as disclosed herein. The insertion depth, which is plotted in millimeters, is also shown in insertion stages (stages 1 through 5), where stage 1 represents the earliest (and most shallow) portion of the insertion process and stage 5 represents the latest (and deepest) portion of the insertion process. FIG. 5 shows plots 604A, 604B and 604C, which each represent a plot from data taken upon the insertion of a non-vibrating insertion tool, such as those present in the prior art. The three plots 604A, 604B and 604C differ in that the data to create each plot was taken during different tests of such a non-vibrating insertion tool. On the other hand, plots 602A, 602B and 602C each represent a plot from data taken upon the insertion of a vibrating insertion tool according to embodiments of the present technology. The three plots 602A, 602B and 602C differ in that the data to create each plot was taken during different tests of such a vibrating insertion tool. As shown in FIG. 5 when comparing plots 604, representing exemplary insertion force data for a non-vibrating insertion tool, and plots 602, representing exemplary insertion force data for a vibrating insertion tool, the insertion force created by a non-vibrating insertion tool is significantly higher than by a vibrating insertion tool in accordance with embodiments of the present technology. More specifically, at each marked insertion depth 1 through 5, the insertion force of the non-vibrating insertion tool is higher than the corresponding insertion force of the vibrating insertion tool at the same insertion depth. For example, the insertion force data for the exemplary non-vibrating insertion tool at insertion depth stage 4 show insertion forces of approximately 0.26 N, 0.24 N and 0.17 N for plots 604A, 604B and 604C, respectively. On the other hand, the insertion force data for the exemplary vibrating insertion tool of the present technology at the same insertion depth stage 4 show insertion forces of approximately 0.08, 0.08 and −0.01 for plots 602A, 602B and 602C, respectively. Therefore, due to the vibrating of the insertion tool instead of a non-vibrating insertion tool, trauma to the cochlea of the recipient due to insertion of a medical device can minimized.

Furthermore, the inventors have further determined that implementing certain specific vibration profiles with the disclosed vibrating insertion tool helps to maximize the effectiveness of the vibrations transferred by the insertion tool to the medical device to be implanted so as to minimize the insertion force necessary, and therefore minimize any trauma experienced by the recipient. For example, a vibration profile may include the axis of vibration (e.g. along an axis longitudinal to the spine, along an axis perpendicular or otherwise transverse to the spine, rotational, or a combination of the three), the amplitude of the vibrations and the frequency of the vibrations, among others. For example, plots 602A, 602B and 602C in FIG. 5 represent data from a vibrating insertion tool according to embodiments of the present technology, as noted, and where the vibration source is vibrating along an axis longitudinal to the spine. Furthermore, plot 602A represents data from such an insertion tool with a vibration profile of 200 Hz frequency and 2 V amplitude, plot 602B represents data from such an insertion tool with a vibration profile of 100 Hz frequency and 2 V amplitude, and plot 602C represents data from such an insertion tool with a vibration profile of 200 Hz frequency and 2 V amplitude. However, there is not one vibration profile that would maximize the effectiveness of the vibrating insertion tool in all surgical situations. Instead, the vibration profiles are variable based on various factors or circumstances. For example, an ideal vibration profile for a certain surgical situation may be influenced by any one or more of the following factors: the type and dimensions of the insertion tool being used, the size of the surgeon's hand, the surgeon's grip on the insertion tool, the geometry of the patient, the type of surgery being performed including the surgeon's manual surgical technique, the fundamental frequency of the tool with the device, the medical device being implanted (e.g. electrode assembly), the insertion technique (e.g. standard insertion technique (SIT), advance off stylet insertion technique (AOS), etc.), the surgical environmental conditions, among other variables. An ideal vibration profile may include a frequency of between 100 Hz and 200 Hz and an amplitude of between 1 V and 2 V. However, ideal vibration profiles may extend outside of those ranges. A surgeon using the vibrating insertion tool may adjust the vibration profile during surgery when one or more of the factors changes over time. This surgeon adjustment is discussed further with respect to FIG. 6B.

Figure 6A:
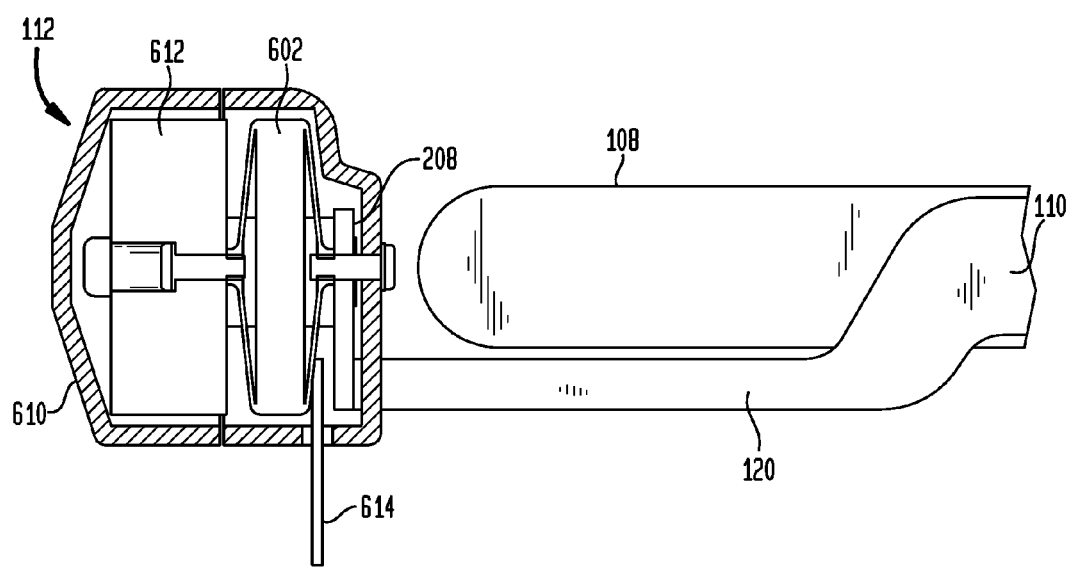
FIG. 6A is a cross-sectional view of a vibration source and its physical relationship with a junction of an exemplary insertion tool and spine member, according to embodiments of the present technology.

FIG. 6A is a close-up cross-sectional view of vibration source 112 and its physical relationship with junction 108 of an exemplary insertion tool and spine member 110, according to embodiments of the present technology. As noted, spine member 110 is coupled to vibration source 112 such that vibrations from vibration source 112 are transferred to spine member 110. As shown in FIG. 6A, spine member 110 is connected to vibration source 112 via plate 208. Referring back to FIG. 2, spine member 110 may be connected to a vibration source holder 222, which includes plate 208, and secures vibration source 112 in place with respect to spine member 110. However, spine member 110 may be connected to vibration source 112 using a variety of different techniques, as would be understood by a person of ordinary skill in the art.

Vibration source 112 includes a housing 610, a mass 612 and a vibrating transducer 602, where mass 612 and transducer 602 are located inside housing 610. It may be desirable to couple a mass to the transducer to facilitate operation of the device and increase the amplitude of motion induced by the transducer. Transducer 602 is coupled to plate 208 such that when transducer 602 vibrates, it transfers such vibrations to plate 208 and subsequently to spine member 110. Vibration source 112 also includes a conductive element 614 that extends from the inside of housing 610 of vibration source 112 to the outside of housing 610. Conductive element 614 may be a wire or any other element that is configured to carry driver and/or control signals into the vibration source, for example to drive transducer 602, from a controller module or other external devices.

Figure 6B:
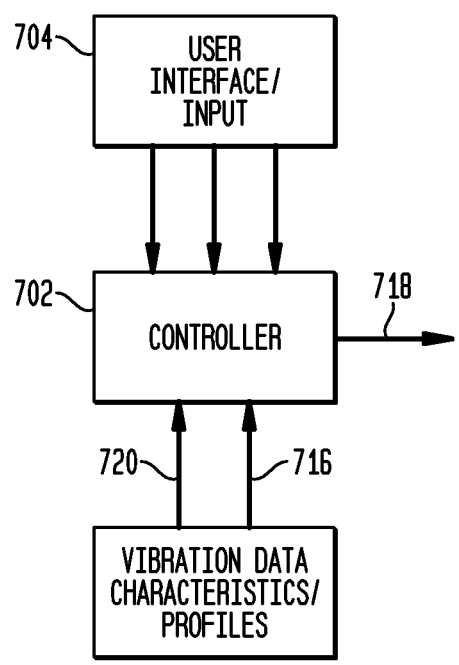
FIG. 6B is a block diagram illustrating the control features, according to embodiments of the present technology.

FIG. 6B is a block diagram illustrating the control features of embodiments of the present technology. As noted, a surgeon using the vibrating insertion tool may adjust the vibration profile during surgery when one or more of the factors changes over time. Controller 702, which may be included in the vibration source 112 itself or may be an external component, controls the characteristics of the vibration source 112. For example, controller 702 sends driver or control signals 718 to vibration source 112 to instruct vibration source 112 as to the vibration characteristics that vibration source 112 should implement. Driver or control signals 718 may be sent from the controller 702 to vibration source 112 via, for example, conductive element 614.

As shown in FIG. 6B, controller 702 receives inputs from two different sources. First, controller 702 receives inputs from a user interface 704. User interface 704 may include any set of buttons, switches, joysticks, controls or other interface that allows a user to enter information into the system. Second, controller 702 receives inputs from stored vibration data characteristics, or vibration profiles. Alternatively, vibration profiles may be stored directly in controller 702. User interface 704 may be used by the surgeon to adjust the characteristics of the surgery being performed and/or to directly change the vibration profile being implemented by the vibration source. If user interface 704 is used to adjust the characteristics before a surgery, such characteristics may be used by the controller to select an initial vibration profile 716 to be used during surgery.

However, if the surgeon recognizes a change in circumstances during the surgery, such as the intricacies of a patient's body, then the surgeon may choose to adjust the vibration profile during surgery. As noted, there is not one vibration profile that would maximize the effectiveness of the vibrating insertion tool in all surgical situations. Since certain specific vibration profiles help to maximize the effectiveness of the vibrations implemented by the insertion tool so as to minimize any trauma experienced by the recipient, the applicable vibration profile may change with a change in surgical circumstances. Accordingly, the vibration profiles are variable based on various factors. Therefore, the surgeon may recognize a change in circumstances, or surgical situation, such that a different vibration profile would be be more effective for those new circumstances. As noted, various factors/circumstances may change during surgery, such as the type and dimensions of insertion tool being used, the surgeon's grip on insertion tool, the geometry of the patient, surgical technique, environmental conditions in and around the patient, among others. Therefore, the user interface 704 may be used to adjust the characteristics during a surgery, such characteristics may be used by the controller to automatically implement a different, or adjusted, vibration profile 720 on the fly. For example, if the surgeon adjusts the type of surgery being performed, one aspect of the vibration profile, such as the amplitude or frequency of the vibration profile, may change to adjust for the change in surgery circumstances. The surgeon may also directly select a different vibration profile if the surgeon knows which vibration profile will be most effective for the new circumstances. After a new vibration profile has been adjusted/selected, the controller 702 will send new driver/control signals 718 to drive the vibration source 112 based on the adjusted vibration characteristics.

For example, referring back to FIG. 5, the vibration profile used to yield insertion force data represented by plot 602C may minimize the insertion forces applied to the recipient's cochlea structures in a certain set of circumstances. However, the vibration profile used to yield insertion force data represented by plot 602A or 602B may minimize the insertion forces applied to the recipient's cochlea structures in different surgical circumstances.

The technology described and claimed herein is not to be limited in scope by the specific preferred embodiments herein disclosed, since these embodiments are intended as illustrations, and not limitations, of several aspects of the technology. Any equivalent embodiments are intended to be within the scope of this technology. Indeed, various modifications of the technology in addition to those shown and described herein will become apparent to those skilled in the art from the foregoing description. Such modifications are also intended to fall within the scope of the appended claims.

What is claimed is:

1. A vibrating insertion tool comprising:
an insertion tool controllable by a user to support and guide movement of an object, the insertion tool comprising an elongate arm having a proximal end region and a distal end region, the distal end region having a receiving region;
a user-controllable vibration source for generating vibrations in accordance with a selected vibration profile; and
an elongate rigid spine, connected to the vibration source, configured to deliver the vibrations to the receiving region,
wherein the insertion tool is a cochlear electrode array insertion tool, and the insertion tool includes a second arm, wherein the elongate arm and the second arm articulate relative to one another so as to move respective tip sections of the tool towards each other to grip and hold the electrode array for insertion into a cochlear, and wherein open space is present between the elongate arm and the elongate rigid spine at all locations away from a respective tip section of the elongate arm, and wherein open space is present everywhere between the elongate rigid spine and the second arm.

2. The vibrating insertion tool of claim 1, wherein the spine is configured to deliver the vibrations to the receiving region in accordance with a vibration profile that is substantially the same as the selected vibration profile.

3. The vibrating insertion tool of claim 1, wherein the selected vibration profile is actively adjustable by the user.

4. The vibrating insertion tool of claim 1, further comprising a user interface configured to receive instructions from the user related to the vibration profile.

5. The vibrating insertion tool of claim 4, wherein the vibration source automatically generates second vibrations based on a second vibration profile based on the received instructions.

6. The vibrating insertion tool of claim 1, further comprising a separator connected to the elongate arm and connected to the spine.

7. The vibrating insertion tool of claim 6, wherein the separator is flexible.

8. The vibrating insertion tool of claim 1, wherein the spine is substantially mechanically isolated from the arm.

9. The vibrating insertion tool of claim 8, wherein the spine is mechanically isolated from the proximal end region of the elongate arm.

10. The vibrating insertion tool of claim 1, wherein the spine is connected to a vibration source holder that couples the spine to the vibration source.

11. The vibrating insertion tool of claim 1, wherein the object is an electrode assembly of a cochlear implant.

12. The vibrating insertion tool of claim 1, wherein the vibration source is a sonic transducer.

13. The vibrating insertion tool of claim 1, wherein the vibration source is configured to vibrate within a range having a maximum value of 200 Hz.

14. The vibrating insertion tool of claim 1, wherein the spine extends a length at least about the same as the length of the insertion tool.

15. The vibrating insertion tool of claim 1, wherein the spine supports the vibration source at a location remote from the insertion tool.

16. The vibrating insertion tool of claim 1, wherein the spine extends from a distal location of the insertion tool to at least a location proximal the insertion tool.

17. The vibrating insertion tool of claim 1, wherein the elongate rigid spine extends between the elongate arm and the second arm from the tip of the elongate arm, the tip of the elongate arm being at a distal end of the tool, and wherein the elongate rigid spine also includes a portion that dog legs outward away from between the elongate arm and the second arm to a side of the arms, after which the elongate rigid spine extends along a side of the arms to the vibration source.

18. The vibrating insertion tool of claim 1, wherein the insertion tool is configured to be held in use by a surgeon at a location at a middle of the elongate arm and at a location at a middle of a second arm, wherein the insertion tool is a tool that makes use of two third-class levers connected at one fixed end corresponding to the fulcrum point of each lever with pincers at an end opposite the one fixed end, wherein the two levers correspond to the elongate arm and the second arm, and wherein the insertion tool is configured such that respective forces applied to the two levers in a direction towards each other moves the pincers towards each other.

19. A vibrating insertion tool comprising:
an insertion tool controllable by a user to support and guide movement of an object, the insertion tool comprising an elongate arm having a proximal end region and a distal end region, the distal end region having a receiving region;
a user-controllable vibration source for generating vibrations in accordance with a selected vibration profile; and
an elongate rigid spine, connected to the vibration source, configured to deliver the vibrations to the receiving region,
wherein the insertion tool is a tweezers, and
wherein the elongate rigid spine extends between two arms of the tweezers from a tip of the elongate arm, the elongate arm being one of the two arms of the tweezers, the tip being at one of two pincers of the tweezers, and wherein the elongate rigid spine also includes a portion that dog legs outward away from between the two arms to a side of the two arms, after which the elongate rigid spine extends along a side of the arms to the vibration source.

20. The vibrating insertion tool of claim 19, wherein the insertion tool is a cochlear electrode array insertion tool, and the insertion tool includes a second arm, wherein the second arm is the other of the two arms of the tweezers, wherein the elongate arm and the second arm articulate relative to one another so as to move respective tip sections of the arms towards each other to grip and hold the electrode array for insertion into a cochlear, and wherein open space is present between the elongate arm and the elongate rigid spine at all locations away from the tip section of the elongate arm, and wherein open space is present everywhere between the elongate rigid spine and the second arm.

21. The vibrating insertion tool of claim 19, wherein the elongate rigid spine extends between the elongate arm and a second elongate arm of the tweezers from a tip of the elongate arm, the tip forming one of two pincers of the tweezers.

22. The vibrating insertion tool of claim 19, wherein the elongate rigid spine is isolated from the elongate arm and a second arm of the tweezers at the locations away from a tip of the elongate arm.

23. A cochlear electrode array insertion tool, comprising:
an apparatus configured to releasably grip and support and move the cochlear electrode array during insertion of the cochlear electrode array into a cochlea; and
a vibrator, wherein
the cochlear electrode array insertion tool includes a handle comprising a first handle region and a second handle region,
the apparatus includes a first surface and a second surface at a distal portion of the tool, wherein the cochlear electrode array insertion tool is configured to move the first surface and the second surface relative to each other from human hand input from the handle regions as a result of the handle being extensions of the apparatus configured to releasably grip and support and move the cochlear electrode array,
wherein the first handle region and the second handle region articulate relative to one another so as to respectively move the first surface and the second surface towards each other to grip and hold the electrode array for insertion into a cochlear,
wherein the insertion tool includes an elongate rigid spine, connected to the vibrator configured to deliver the vibrations to the distal portion of the tool, and
wherein open space is present between the first handle region and the elongate rigid spine at all locations away from a respective tip section of the insertion tool, and wherein open space is present everywhere between the elongate rigid spine and the second handle region.

24. The tool of claim 23, wherein the apparatus configured to releasably grip and support and move the cochlear electrode array is a manually actuated apparatus.

25. The tool of claim 23, wherein the apparatus configured to releasably grip and support and move the cochlear electrode array is a tweezers.

* * * * *